(12) United States Patent
Schärer-Brodbeck

(10) Patent No.: US 7,833,703 B2
(45) Date of Patent: Nov. 16, 2010

(54) METHOD FOR THE CONSTRUCTION OF RANDOMIZED GENE SEQUENCE LIBRARIES IN CELLS

(75) Inventor: Claudia Schärer-Brodbeck, Pratteln (CH)

(73) Assignee: ESBATech, an Alcon Biomedical Research Unit, LLC, Schlieren (CH)

( * ) Notice: Subject to any disclaimer, the term of this patent is extended or adjusted under 35 U.S.C. 154(b) by 576 days.

(21) Appl. No.: 10/552,219

(22) PCT Filed: Apr. 11, 2003

(86) PCT No.: PCT/IB03/01452

§ 371 (c)(1), (2), (4) Date: Jun. 29, 2006

(87) PCT Pub. No.: WO2004/090139

PCT Pub. Date: Oct. 21, 2004

(65) Prior Publication Data

US 2007/0298466 A1    Dec. 27, 2007

(51) Int. Cl.
- C12Q 1/68 (2006.01)
- G01N 33/53 (2006.01)
- C12N 15/00 (2006.01)
- C12N 1/19 (2006.01)
- C12N 15/63 (2006.01)

(52) U.S. Cl. .......................... 435/6; 435/7.1; 435/69.1; 435/254.2; 435/320.1

(58) Field of Classification Search .................. None
See application file for complete search history.

(56) References Cited

U.S. PATENT DOCUMENTS 6,410,271 B1    6/2002   Zhu et al.

2002/0160380 A1    1/2002   Truan et al.

FOREIGN PATENT DOCUMENTS

WO    WO 02/00729    1/2002

OTHER PUBLICATIONS

Butler et al. Intracellular expression of *Kluyveromyces lactis* toxin gamma subunit mimics treatment with exogenous toxin and distinguishes two classes of toxin-resistant mutant. Yeast 7: 617-625, 1991.*
Sherman. Getting Started with Yeast. Methods Enzymol. 350:2-41, 2002.*
Monschau et al. Threonine aldolase overexpression plus threonine supplementation enhanced riboflavin production in *Ashbya gossypii*. Applied and Envtl. Microbiol. 64(11): 4283-90, 1998.*
Jirholt et al. Exploiting sequence space: shuffling in vivo formed complementarity determining regions into a master framework.Gene 215: 471-476, 1998.*
Meinhardt et al., "A Novel Approach to Express a Heterlogous Gene on *Kluyveromyces lactis* Linear Killer Plasmids: Expression of the Bacterial *aph* Gene from a Cytoplasmic Promoter Fragment without In-Phase Fusion to the Plasmid Open Reading Frame," *Plasmid* 32, 318-327 (1994).
International Search Report dated Aug. 5, 2003 for corresponding PCT application No. PCT/IB03/01452.
International Preliminary Examination Report dated Aug. 6, 2005 for corresponding PCT application No. PCT/IB03/01452.

* cited by examiner

*Primary Examiner*—Michele K Joike
(74) *Attorney, Agent, or Firm*—Jason J. Derry

(57) ABSTRACT

An in vivo method for the construction of randomized gene libraries and/or domain replacement in gene libraries by homologous recombination using a *Kluyveromyces lactis* killer toxin, in particular the (γ-subunit of the *K. lactis* killer toxin, as negative selection marker is described. The use of the (γ-subunit of *K. lactis* as negative selectable marker increases the percentage of randomized clones.

25 Claims, 4 Drawing Sheets

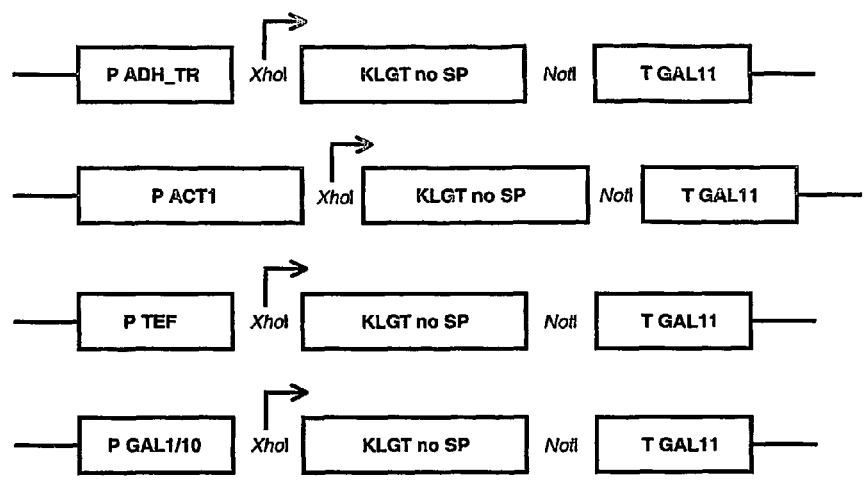
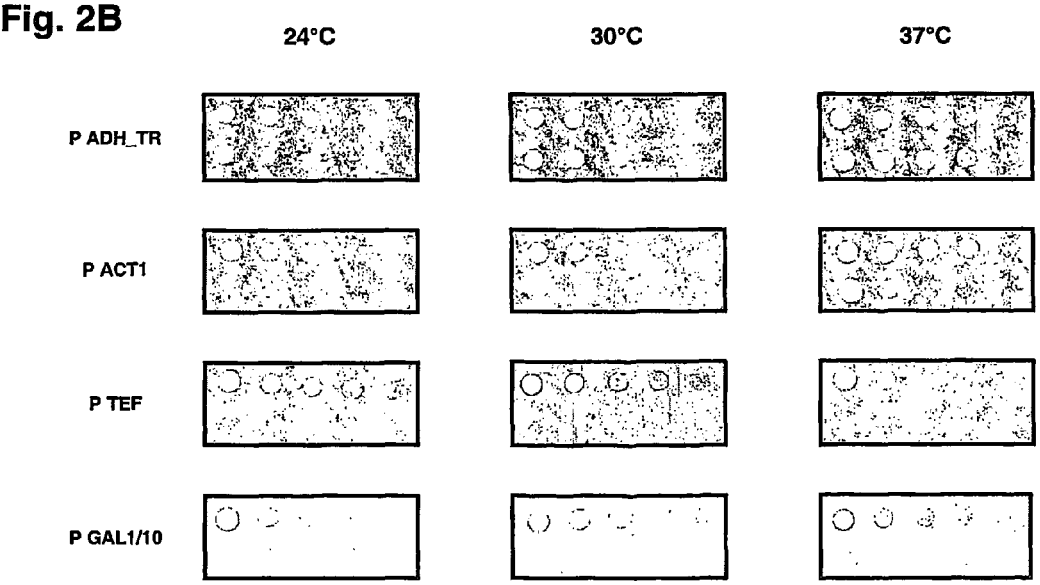

METHOD FOR THE CONSTRUCTION OF RANDOMIZED GENE SEQUENCE LIBRARIES IN CELLS

RELATED APPLICATIONS

This application is the U.S. National Phase Application pursuant to 35 U.S.C. §371 of International Patent Application Serial No. PCT/IB2003/001452 filed Apr. 11, 2003. The entire disclosure of the foregoing application is incorporated herein by reference in its entirety.

TECHNICAL FIELD

The present invention provides an in vivo method for the generation of randomized gene libraries by means of homologous recombination wherein the *Kluyveromyces* lactis killer toxin is used as negative selectable marker.

BACKGROUND ART

For functional studies, it is crucial to analyze individual regions of a protein systematically. This is usually performed by randomizing all amino acids of the region or by varying few conserved positions depending on the size of the region of interest. On one hand, such data results in the identification of key amino acids determining the interaction of a protein region for example with another protein region, with DNA, or with lipid structures. On the other hand, expression in a cellular environment of either a randomized protein region alone or of a randomized region in the context of a full protein directly contributes to the understanding of the protein's function. Another application of region randomization is changing the binding properties of a single chain antibody (scFv). A scFv consists of variable regions of both the light and heavy chain. Each chain features three variable regions, called CDR1, CDR2, and CDR3. Of the six CDRs, the CDR3 of the heavy chain is the major determinant of the scFv's affinity for its antigen. For changing the binding properties of a scFv, the heavy chain CDR3 region of a scFv with a given interaction profile is randomized and screened against the epitope of interest. This usually leads to the identification of scFvs with a low affinity. For improving the affinity, the light chain CDR3 of the novel scFv is then randomized. Therefore, stepwise randomization of two scFv variable regions can be used to isolate new or better binders against a given epitope.

The classical protocol for region replacement/randomization in the context of library production is performed usually in bacteria such as *E. coli*. It involves production of PCR fragments representing the library of regions, digestion with restriction enzymes cutting at or close to the end of the fragments of interest, and ligation into a vector linearized with matching restriction enzymes.

For use in yeast, libraries have been produced directly in yeast with homologous recombination (Hua, Luo et al. 1998). The process requires production of a donor DNA fragment bearing on each end homologies to the linearized target vector. Fragments for use in homologous recombination can therefore be produced by PCR with primers bearing the homologous sequences at their 5' ends.

US patent application published under No. US2002/012734 describes a method for directed evolution, gene reassembly and directed mutagenesis using homologous recombination and selectable markers for counterselection in bacteria.

Although there exist already methods for the construction of randomized gene sequence libraries by means of homologous recombination in cells, there is still a need for methods which allow an efficient construction and selection of such randomized libraries.

DISCLOSURE OF THE INVENTION

Hence it is a general object of the present invention to provide a method for the construction of randomized gene libraries in cells. Said method comprises the following steps:

introducing into suitable host cells capable of homologous recombination a) a target vector comprising at least a first DNA sequence coding for at least a γ-subunit of a *Kluyveromyces lactis* killer toxin as negative selection marker, said DNA sequence being flanked at its 5' end by a first target sequence and at its 3' end by a second target sequence and b) a donor DNA sequence which is flanked, at its 5' end by a DNA sequence which is homologous to said first target sequence and flanked at its 3' end by a DNA sequence which is homologous to said second target sequence and cultivation of said host cells under suitable conditions allowing the selection of host cells in which said DNA sequence in the target vector encoding at least a γ-subunit of a *K. lactis* killer toxin has been replaced by said donor sequence by means of homologous recombination thereby abolishing expression of said γ-subunit of a *K. lactis* killer toxin.

In a preferred embodiment said target vector further comprises a second DNA sequence which encodes at least one protein region, preferably more than two protein regions of a protein of interest, more preferably a full length protein.

In a further preferred embodiment said first DNA sequence of the target vector which comprises at least the coding region of the γ-subunit of the *K. latics* killer toxin and said two flanking regions, replaces a DNA sequence of said second DNA sequence which encodes a protein region.

In another preferred embodiment of the present invention, said DNA sequence encoding at least the γ subunit of the *K. lactis* killer toxin is under transcriptional control of a heterologous promoter, preferably a constitutive promoter, more preferably a TEF promoter from *Ashbya gossypii*.

In a further preferred embodiment said promoter is located between the DNA sequence encoding at least the γ-toxin subunit of *K. lactis* killer toxin and one of the two target sequences for homologous recombination.

In a further preferred embodiment said first DNA sequence of said target vector comprises a unique recognition site for a restriction enzyme. Said unique recognition site is preferably located in the coding region of the γ-toxin DNA sequence or more preferably between the coding region of the γ-toxin DNA sequence and the promoter driving transcription of the γ-toxin subunit.

In still another preferred embodiment said second DNA sequence of said target vector encodes an antibody or a single chain antibody (scFv).

In a much preferred embodiment of the present invention said first DNA sequence of said target vector replaces a DNA sequence in said second DNA sequence of said target vector which comprises at least the coding region of a CDR region of an antibody or a single chain antibody, preferably a CDR3 region, more preferably a CDR3VL region, even more preferably a CDR2 and a CDR3 region.

A further preferred embodiment relates to a method in which said first DNA sequence of said target vector comprising at least the γ-subunit of a *K. lactis* killer toxin is transcribed in the opposite direction than said antibody or single chain antibody gene.

In a further much preferred embodiment of the present invention said γ-toxin subunit of the *K. lactis* killer toxin lacks the signal peptide (referred to as "KLGT") and said host cells are yeast cells, preferably *Saccharomyces cerivisiae* cells.

In still another preferred embodiment of the present invention said target vector is introduced into said host cells in linearized form. The linearization of said target vector is preferably achieved by cutting said first DNA sequence of said target vector at said unique recognition site.

In a further preferred embodiment said donor DNA sequence comprises a DNA sequence encoding a protein region, preferably a CDR region of an antibody or a scFv.

The target vector and said donor sequence are preferably introduced into said host cells by co-transformation, more preferably said target vector is co-transformed into said cells with a molar excess of said donor sequence, even more preferably with at least a 25 times molar excess of said donor sequence, more preferably at least 40 times molar excess.

In yet a further preferred embodiment of the present invention said yeast host cells are cultivated at a temperature selected from the range of 24° C. to 30° C., preferably at 24° C. Said temperatures allow the selection of host cells in which the desired replacement of the negative selectable marker in the target vector by the donor sequence has occurred.

Another aspect of the present invention relates to a DNA vector which comprises the following sequences: a first target sequence for homologous recombination, a TEF promoter from *Ashbya gossypii*, a DNA sequence encoding at least a γ-subunit of a *K. lactis* killer toxin and a second target sequence for homologous recombination.

A further aspect of the present invention is directed to a host cell, preferably a yeast cell, more preferably a *S. cerevisiae* cell, comprising a DNA vector of the present invention.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 2A shows constructs for expression of the γ-toxin of the *Kluyveromyces lactis* killer toxin γ-subunit in *Saccharomyces cerevisiae*, FIG. 2B shows that expression of the γ-toxin is lethal above a protein threshold and at a temperature of 30° C. or below.

MODES FOR CARRYING OUT THE INVENTION

Figure 1A:
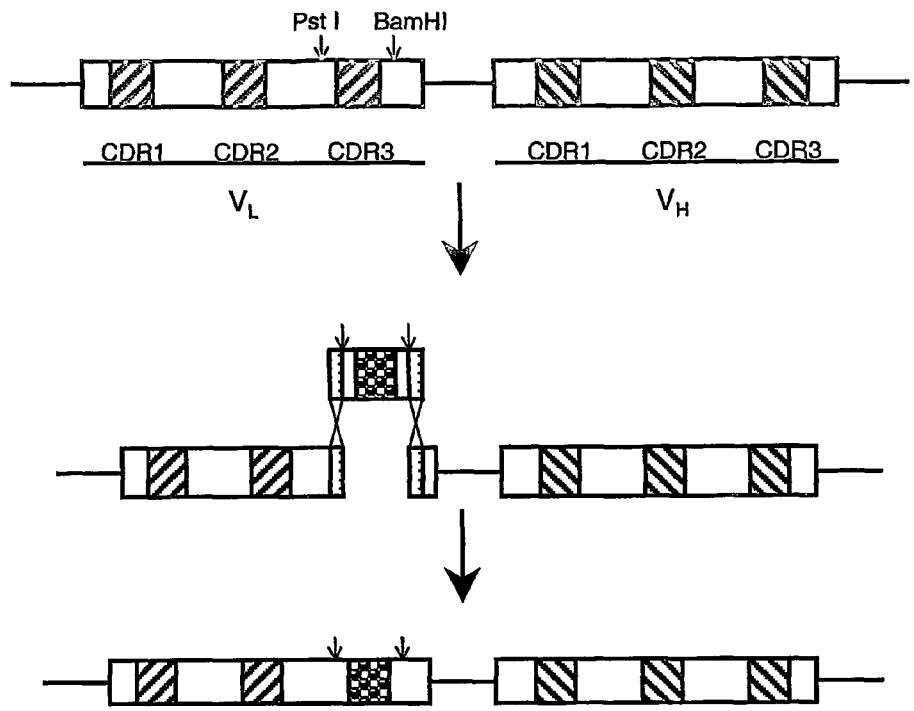
FIG. 1A shows a strategy for protein region replacement using homologous recombination in yeast.

The method of the present invention for protein region replacement and/or randomization using homologous recombination in cells, preferably yeast cells, coupled to a counterselection for non-recombining clones offers important advantages over existing systems designed for the same purpose. First, in contrast to library production using cloning or straight homologous recombination, the negative selection protocol keeps the background of non-randomized clones below 0.5%, which may be essential in certain applications. In contrast to library production with cloning, the library can be produced and screened in one single step in yeast. The loss of poorly growing clones encountered during bacterial library production is therefore eliminated. In addition, the libraries produced with homologous recombination can be stored infinitely as a yeast glycerol stock, which allows direct use in a next screening experiment. And, as, for libraries produced in bacteria, the libraries produced in yeast can also be used for experiments in other; organisms.

In the scope of the present invention it, was: now found that the *Kluyveromyces lactis* killer toxin γ-subunit (referred to as γ-toxin) can be used as a negative selection marker in a method for the generation of randomized gene libraries. When a correct homologous recombination occurs between the target vector DNA comprising the coding sequence of the γ-subunit of *K. lactis* killer toxin and a donor sequence, the negative selection marker is looped out thereby allowing cell survival. In the case of vector background or non-homologous recombination the presence of the negative selection marker leads to cell death It has been shown that the *K. lactis* killer toxin leads to irreversible G1 arrest and loss of viability in sensitive cells, among which are species of *Saccharomyces, Candida, Kluyveromyces*, and *Zyugosaccharomyces*. The α- and β-subunits of the trimeric killer toxin are responsible for entry of the γ-subunit into sensitive cells probably by interacting with the cell wall chitin (Takita and Castilho-Valavicius 1993). The γ-subunit alone, either when expressed extracellularly together with the α- and β-subunits or when expressed conditionally intracellularly, causes the observed G1 arrest (Butler, White et al. 1991), (Butler, White et al. 1994) by interfering with the function of RNA polymerase II in a complex and still poorly understood pathway. Importantly, toxicity of the γ-subunit does not affect the membrane potential, in contrast to most other killer toxins that act as ionophores. Another suitable toxin for use in the method of the present invention is the procaryotic protein Kid (G. de la Cueva-Méndez et al., EMBO J., Vol. 22, No. 2, pp. 246-251, 2003).

The term "DNA sequence encoding a γ-subunit of the *K. lactis* killer toxin" comprises all DNA sequence variations which encode a functional γ-subunit i.e. a γ-subunit which leads to loss of viability in sensitive cells. Said term also includes functional fragments of said γ-subunit.

The term "region" as used herein encompasses any stretch of amino acids and includes protein regions such as e.g. protein domains, partial protein domains as well as fragments thereof.

The term "antibody" as used herein includes both intact antibody molecules and antibody fragments (including Fab, F (ab'), Fv, and F (ab')$_2$).

The construction of DNA vectors used in the present invention and the generation of donor DNA sequence constructs can be done using standard molecular biology techniques as described e.g. in Sambrook J. and Russell D. W., Molecular Cloning: A Laboratory Manual, New York: Cold Spring Harbor Laboratory Press, 2001).

The length of the two target sequences flanking the DNA sequence encoding at least the γ-subunit of the *K. lactis* killer toxin and the homologous sequences comprised in the donor sequence can vary. Usually, a target sequence has a length of about 35 bp to 60 bp. Said length can depend on the specific application, specific gene or regions used in a method of the present invention. The person skilled in the art is able to find the optimal length for a specific gene or region by applying general molecular biology methods and routine experimentation.

The method of the present invention can e.g. be used in region randomization, which is not restricted to the variable regions of antibodies, but can be expanded to any protein region, in particular any small protein region. It requires that the donor DNA fragment be randomized in its central part while still preserving the sequence homologies to the target vector at its ends. The randomization of the central part of the donor sequence can be done by known general molecular biology methods as e.g. described in in Sambrook J. and Russell D. W., Molecular Cloning: A Laboratory Manual, New York: Cold Spring Harbor Laboratory Press, 2001).

The introduction of the vector/DNA constructs described in the present invention into suitable host cells can be done by standard methods such as e.g. chemical transformation, electroporation. The host cells are cultivated under standard conditions and in standard culture media known to a person skilled in the art.

The invention is now further illustrated by means of examples.

Replacement of the CDR3L of a Prototype Single Chain using Homologous Recombination in Yeast The structure of a prototype single chain (scFv) is depicted in FIG. 1A. It consists of a light VL and a heavy VH chain connected to each other with a flexible linker part. Each chain features three variable regions, called CDR1, CDR2, and CDR3. Of the six CDRs, the CDR3 of the heavy chain is the major determinant of the scFv's affinity for its antigen. For generation of a high-affinity scFv, the CDR3 of VH is randomized in a library and the best binder identified in an assay. The affinity of the identified scFv is further improved by randomizing the CDR3 of VL. Randomization of the latter involves three amino acids and therefore requires a library complexity of 8000 independent clones. This low complexity and the prospect of producing and screening the library in one step directly in yeast prompted us to randomize the CDR3 of VL using homologous recombination.

Figure 1B:
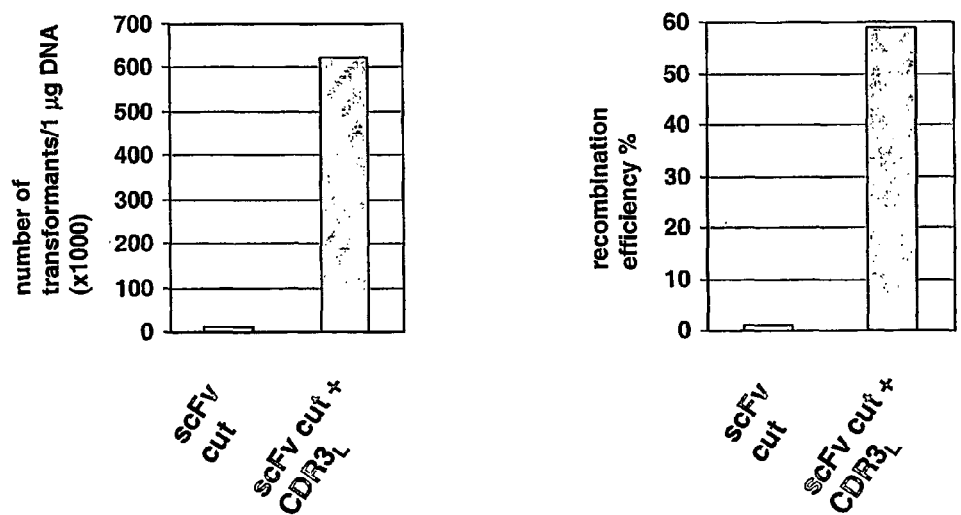
FIG. 1B shows that protein region replacement is highly efficient using homologous recombination.

To test the feasibility of such an idea (FIG. 1A), the CDR3 of the light chain of the scFv on plasmid pVKS1/25 was removed using PstI and BamHI restriction enzymes, which cut 30 and 80 by from the CDR3 VL, respectively (FIG. 1A). The linearized vector was dephosphorylated using calf intestine phosphatase prior to its use as a target sequence in the recombination experiment. The donor DNA fragment CDR3 VL was produced by PCR using oligonucleotides CDR3f_40 (SEQ ID NO: 1) and CDR3r_60 (SEQ ID NO: 2) and the scFv of pVKS1/25 as template; it started 40 by upstream of the PstI site and terminated 60 by downstream of the BamHI site therefore providing homologies for recombination and also spanning the full CDR3 VL sequence that had been removed in the target sequence. For homologous recombination, 100 ng of the linearized vector were co-transformed with a 40× molar excess of donor DNA fragment into the yeast strain JPY9. As a negative control, 100 ng of linearized vector without donor DNA fragment were transformed. Following transformation, the cells were spread onto selective plates and incubated at 24° C. until transformants were readily visible. The growing colonies were then counted and the number of transformants per microgram DNA calculated (FIG. 1B, a). Co-transformation of linearized target vector and donor DNA resulted in ~623'000 clones (scFv cut+CDR3L) whereas transformation of linearized vector only yielded ~10'500 transformants (scFv cut) considered to be vector background. The recombination efficiency was then calculated as the ratio of the number of transformants formed upon co-transformation of target and donor DNA divided by the number of transformants formed upon transformation of target DNA only (FIG. 1B,). It was found that the number of transformants was stimulated 59× when donor DNA was included in the reaction. Restriction analysis of the clones formed upon co-transformation of target and donor DNA revealed that 37 out of 37 clones had recombined the CDR3 VL donor DNA into the target vector, which is in support of the calculated recombination efficiency. Sequencing confirmed that more than 95% of the analyzed clones had performed the recombination event correctly; the remaining 5% of the clones, even though integration occurred at the correct site, showed one or two by deletions close to the recombination junctions.

In summary, it can be concluded that integration of a donor DNA sequence into a target sequence of choice is highly efficient. The procedure described above can easily be adapted for randomization of a small protein region such as the CDR3 VL. Based on the number of transformants formed per microgram DNA, it can be assumed that randomization of five amino acids requiring a library with a complexity of $1.6 \times 10^6$ clones can be achieved using homologous recombination. In addition, the vector background is in the range of 1.5% of the total clones, which is lower than what is expected for classical library cloning.

Expression of the *Kluyveromyces lactis* Killer Toxin γ-Subunit in *Saccharomyces cerevisiae*

Figure 3:
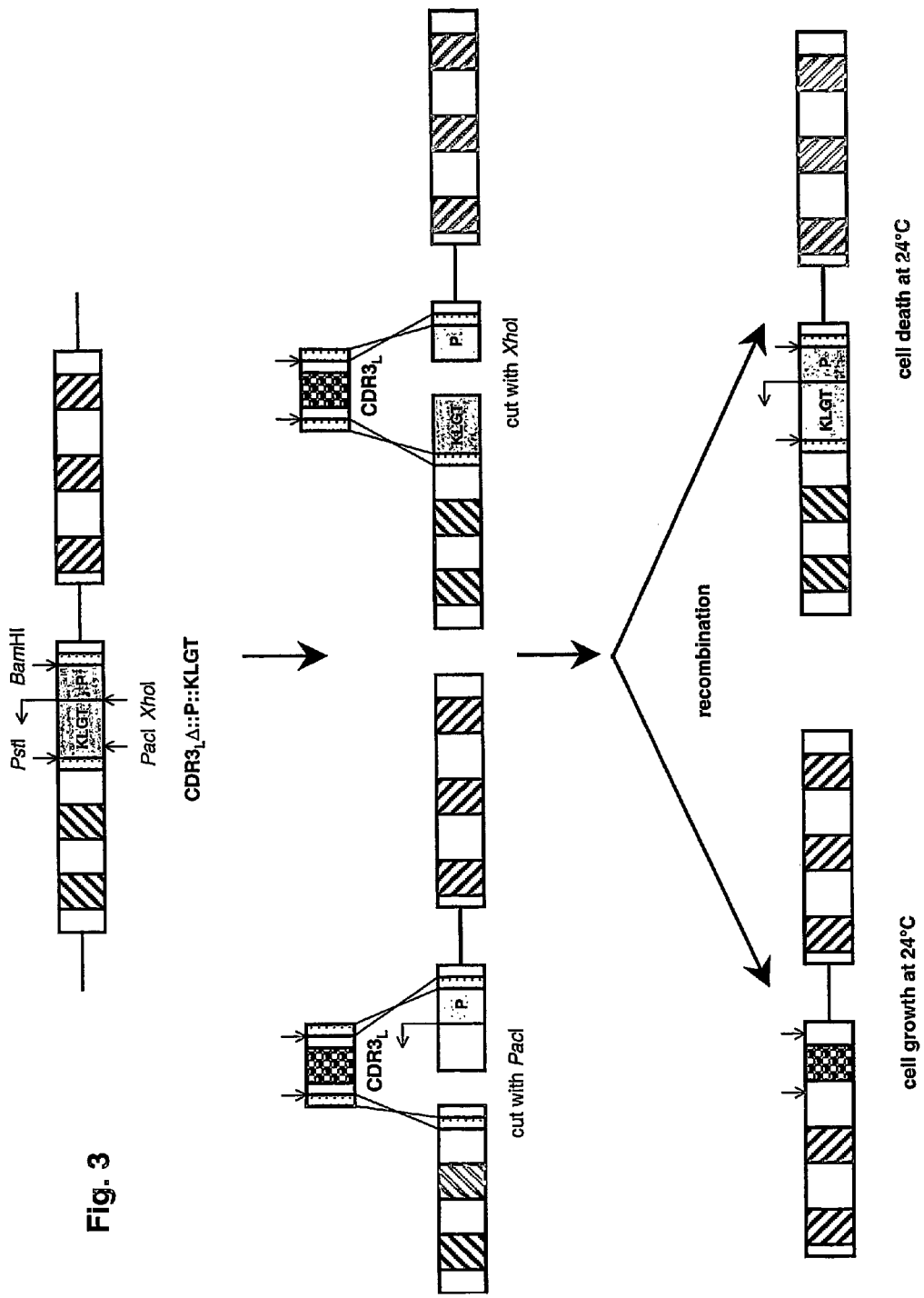
FIG. 3 shows domain replacement strategy on a prototype single chain using the γ-toxin as a negative selection marker.

For some applications, it is crucial that the vector background be as low as possible, optimally below 1%. One such example is improving the binding affinity of a scFv for a given epitope. This is performed by randomizing the CDR3 VL of a weak binder and selecting for binders with higher affinity. Since the background clones in such a situation are binders, even though weak ones, they would interfere with the selection of improved binders. The inventors therefore thought of including a negative selection marker in the target vector DNA that would be looped out if correct homologous recombination occurred and that would result in cell death in the case of vector background or non-homologous recombination (FIG. 3). The *Kluyveromyces lactis* killer toxin γ-subunit (referred to as γ-toxin) was identified as a suitable negative selection marker. It has been shown that the *K. lactis* killer toxin leads to irreversible G1 arrest and loss of viability in sensitive yeast cells, among which are species of *Saccharomyces, Candida, Kluyveromyces,* and *Zygosaccharomyces*. The α- and β-subunits of the trimeric killer toxin are responsible for entry of the γ-subunit into sensitive cells probably by interacting with the cell wall chitin (Takita and Castilho-Valavicius 1993). The γ-subunit alone, either when expressed extracellularly together with the α- and β-subunits or when expressed conditionally intracellularly, causes the observed G1 arrest (Butler, White et al. 1991), (Butler, White et al. 1994) by interfering with the function of RNA polymerase II in a complex and still poorly understood pathway. Importantly, toxicity of the γ-subunit does not affect the membrane potential, in contrast to most other killer toxins that act as ionophores.

Prior to use of the γ-toxin as a negative selection in the recombination process, the inventors wanted to determine the sensitivity of their standard yeast strains JPY5 and JPY9 to intracellular expression of the toxin. To do so, the γ-toxin lacking the signal peptide (referred to as KLGT) was cloned under control of the weak truncated constitutive ADH1 promoter, under control of the strong constitutive ACT1 and TEF promoters, and under control of the strong inducible GAL1/

10 promoter (FIG. 2A). The resulting constructs and the corresponding plasmid controls were transformed into our Wt yeast strain. Single transformants were chosen, grown in selective liquid medium, and used for serial dilution spotting assays for observing growth properties at 24° C., 30° C., and 37° C. (FIG. 2B). All plasmid controls (upper rows) grew equally well at the three temperatures tested and on either glucose or galactose (for PGAL1/10) selective plates. The γ-toxin expressed from PADH1tr slightly impaired growth at 24° C. without affecting growth at either 30° C. or 37° C. (PADH1tr lower rows). When expressed from the stronger PACT1, the γ-toxin completely abolished growth at both 24° C. and 30° C. and slightly impaired growth at 37° C. (PACT1 lower rows). Using the strong PTEF from Ashbya gossypii (Wach 1996) and the induced, strong PGAL1/10, expression of the γ-toxin was lethal at temperatures selected from the range of 24° C. to 30° C. and severely reduced growth at 37° C. (PTEF and PGAL1/10 lower rows).

It can therefore be concluded that expression of the K. lactis γ-toxin in the yeast strains JPY5 and JPY9 is lethal above a certain threshold protein level and that the activity of the toxin is conditional allowing growth at 37° C. The γ-toxin can therefore be used as a negative marker in the recombination process.

Use of the Killer Toxin γ-Subunit Significantly Reduces Background Growth in Applications using Homologous Recombination In order to make use of the γ-toxin as a negative selection marker, the toxin under control of the yeast ACT1 promoter was integrated into the scFv. For direct comparison of the recombination efficiencies with and without negative selection, the γ-toxin was integrated such as to replace the CDR3 VL (FIG. 3, CDR3LΔ::PACT1:Y:KLGT). To do so, the PstI BamHI fragment spanning the CDR3VL was replaced with the PACT1::KLGT construct using homologous recombination in such a way that the PstI and BamHI sites of the scFv were reconstituted. In order to avoid promoter interference with the PACT1 driving expression of the scFv, the γ-toxin construct was integrated such that it is transcribed in the opposite direction of the scFv gene. Upon linearization of the target vector within the γ-toxin sequence and upon co-transformation of the donor DNA fragment, it is expected that the γ-toxin is looped out in cases where proper homologous recombination occurs resulting in cell growth at 24° C. However, if either there is circular vector background or integration of the donor DNA fragment does not take place, the sequence of the γ-toxin will be intact, the toxin will be expressed, and the corresponding cells will die at 24° C. (FIG. 3).

Figure 4A:
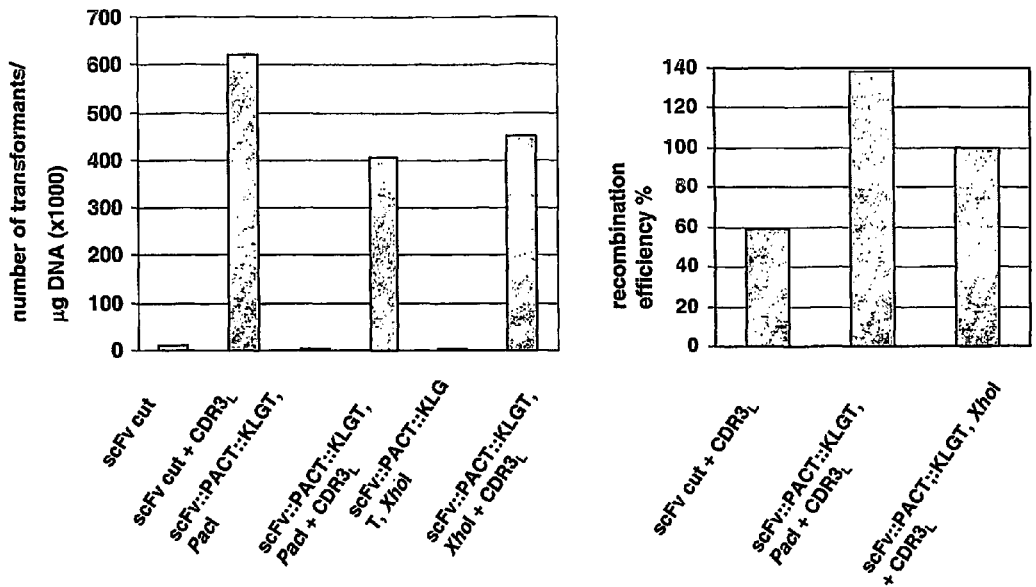
FIG. 4A shows that the use of a PACT1::KLGT negative selection marker significantly reduces background growth in applications using homologous recombination.
Figure 4B:
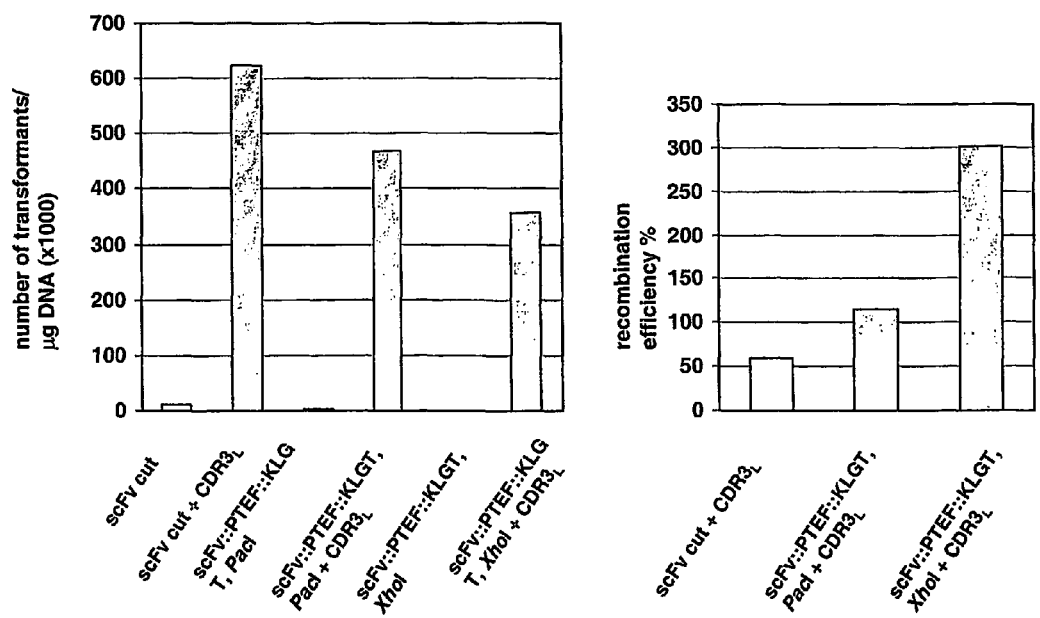
FIG. 4B shows that the use of a PTEF::KLGT negative selection marker significantly reduces background growth in applications using homologous recombination.

The effectiveness of the negative selection in the context of homologous recombination was assayed by comparing integration of the CDR3 VL donor DNA fragment into the linearized scFv target vector without negative selection to its integration into a linearized scFV target vector where the CDR3VL had been replaced with the negative marker. The scFv including the γ-toxin negative marker (scFv::PACT1::KLGT) was either linearized with the restriction enzyme PacI within the coding sequence of the toxin or with the enzyme XhoI that recognizes a site between the promoter and the toxin sequence (FIG. 3). As for the scFv without negative marker, both target vectors were dephosphorylated prior to use. For homologous recombination, 100 ng of each of the linearized vectors were co-transformed with a 40× molar excess of donor DNA fragment into the yeast strain JPY9. As a negative control, 100 ng of each of the linearized vectors without donor DNA fragment were transformed. Following transformation, the cells were spread onto selective plates and incubated at 24° C. until transformants were readily visible. The growing colonies were then counted and the number of transformants per microgram DNA calculated (FIG. 4A). Co-transformation of the scFv::PACT1::KLGT target linearized with PacI and the CDR3 VL donor fragment resulted in ~407'000 colonies; co-transformation of the same target vector linearized with XhoI and the CDR3VL donor DNA yielded ~450,000 transformants. When compared to the number of transformants (~623'000) obtained in the absence of the toxin, a 30% reduction in the transformation efficiency was observed. Transformation of the linearized vectors alone resulted in ~10'500, ~3'000, and ~4'500 colonies for scFv, scFv::PACT1::KLGT cut with PacI, and for scFv::PACT1::KLGT cut with XhoI, respectively. The recombination efficiency increased from 59 fold without negative selection to 138 or 100 fold including negative selection depending on the site of target vector linearization. Restriction analysis of the clones produced upon co-transformation of the target vector with negative selection and the donor DNA indicated that 16 out of 16 clones had recombined properly. There was no difference between the negative selection target vector linearized at PacI or at XhoI with respect to recombination correctness. In the case of target vector linearization with PacI, restriction analysis of the vector background clones showed that closing of the vector occurred by a recombination event at the PacI site. The result is a four bp deletion and therefore a frameshift in the coding sequence of the toxin. If the negative selection vector was linearized with XhoI, it was closed by a dramatic recombination event between the actin promoter found adjacent to the XhoI site and the identical actin promoter driving scFv expression. This massive recombination process loops out the intervening γ-toxin.

The γ-toxin has been used as a negative marker for elimination of non-recombining clones in the context of CDR3VL replacement on a prototype single chain. Three conclusions can be drawn from the presented data. First, the recombination efficiency has been increased by a factor 2 to 2.5 if compared to standard recombinational replacement of the same region. It was observed that the recombination efficiency was higher, if the PACT1::KLGT negative marker was linearized within the coding sequence than between the actin promoter and the toxin sequence. This observation is explained by the fact that in the latter case the actin promoter is found at the recombinogenic ends of the linearized vector. It will therefore recombine preferentially with the actin promoter driving expression of the scFv. This recombination event loops out the intervening toxin allowing cell growth without integration of the donor DNA. Such an event is unlikely to occur upon linearization within the coding sequence of the toxin because the actin promoter driving expression of the toxin is separated from the open, recombinogenic ends by 600 unrelated bp. However, it was observed that the vectors linearized within the coding sequence are closed with a minor recombination event enabled by the specific sequence context around the site of linearization. The resulting toxin lacks four bp within the coding sequence, which renders it catalytically inactive. Cell growth at 24° C. without proper integration of the donor DNA is therefore possible. Based on the calculated recombination efficiencies, we can say that the recombination event between the two identical actin promoters takes place with a higher frequency than the recombination event within the coding sequence of the toxin. The second conclusion relates to the total number of clones per microgram target DNA. It was seen that ~66% of the total transformants were counted for experiments including the negative selection if compared to region replacements performed without negative selection. In the latter approach, only an integration event has to take place. In the former case, the integration event involves in addition the removal of the negative selection marker, which probably accounts for the decreased efficiency. The third conclusion is that the fidelity of recombination is not affected if an intervening sequence has to be looped out for successful integration.

In summary, it can be stated that using the *K. lactis* γ-toxin as negative selection marker for counteracting non-recombining clones reduces the background 2 to 2.5 fold while decreasing the total number of clones produced per microgram target DNA by 30%.

Use of a Heterologous Promoter Driving Expression of the Negative Marker further Reduces Background Even though the vector background was significantly diminished when using a negative marker for controlling the recombination process, the approach described above confronted us with two problems. If the target vector is linearized within the coding sequence of the toxin, it can be closed without integration of the donor DNA in a way that inactivates the toxin's catalytic activity. This allows cell growth without occurrence of the correct recombination event. Another problem is posed by the finding that the actin promoters driving expression of the scFv and the toxin recombine if linearization places the latter at the recombinogenic ends. This results in removal of the intervening toxin and as before cell growth in the absence of a correct recombination event.

By replacing the actin promoter of the γ-toxin with the heterologous PTEF from *Ashbya gossypii*, the inventors hoped to eliminate recombination between the two promoters and thereby further decrease the background. To do so, the PTEF::KLGT fusion was integrated into the prototype scFv such as to replace the CDR3VL (scFv::PTEF::KLGT) as described before (FIG. 3). The novel target vector was linearized as described with PacI within the coding sequence and with XhoI between the promoter and the toxin. 100 ng of each of the linearized vectors were co-transformed with a 40× molar excess of donor DNA fragment into the yeast strain JPY9. As a negative control, 100 ng of each of the linearized vectors without donor DNA fragment were transformed. Following transformation, the cells were spread onto selective plates and incubated at 24° C. until transformants were readily visible. The growing colonies were then counted and the number of transformants per microgram DNA calculated (FIG. 4B). Co-transformation of scFv::PTEF::KLGT linearized with PacI and the donor CDR3VL DNA yielded ~470'000 clones; co-transformation of the donor DNA and the same vector linearized with XhoI produced ~360'000 transformants. The control transformation using the linearized scFv and the donor DNA resulted in ~623'000 colonies. The recombination efficiency was 115 when using the target vector linearized within the coding sequence of the toxin and 302 for use of the target vector linearized between the heterologous promoter and the toxin. When compared to the recombination efficiency obtained with the target vector without the γ-toxin, a two- up to almost 6 fold increase was observed. Restriction analysis of the clones produced in the co-transformation experiments showed that 22 out of 22 clones had looped out the toxin and integrated the CDR3 VL donor DNA at the correct site. Fidelity of the recombination event was not affected regardless of whether the negative selection target vector was linearized with PacI or with XhoI. Analysis of the background clones produced upon transformation of scFv::PTEF::KLGT linearized with PacI indicated closing of the vector by a minor non-homologous recombination event involving the Pac I sequence as seen for scFv::PACT1::KLGT under the same conditions. If the negative selection vector was linearized with XhoI, it was closed by a dramatic recombination event between the TEF promoter found adjacent to the XhoI site and a related sequence in some other part of the vector. As a result, the γ-toxin is removed without integration of the donor DNA.

Region replacement was performed using homologous recombination. The *Kluyveromyces lactis* killer toxin γ-subunit was introduced at the site to be replaced as a negative selection marker. In an attempt to further minimize growth of background clones, the heterologous promoter PTEF was used for driving expression of the γ-toxin instead of an endogenous *S. cerevisiae* promoter. The target vector was then linearized either within the coding sequence of the toxin or between the promoter and the toxin for co-transformation with the CDR3VL donor DNA. It was found that linearization within the coding sequence resulted in a similar recombination efficiency for the actin and the TEF promoter driving expression of the toxin. Closing of the vector without integration of the donor DNA and therefore appearance of the background clones was achieved in both cases with the identical recombination event at the PacI site, which results in a frameshift within the coding sequence of the toxin. This supports the notion that the recombinogenic ends of the linear fragment determine mainly the sites of recombination and not the promoters located 600 bp downstream. If the target vector was linearized between the promoter and the toxin, a recombination efficiency of ~300 was observed for use of the heterologous promoter compared to one of ~100 with the *S. cerevisiae* endogenous actin promoter. Restriction analysis of the rare background clones produced upon transformation of the target vector linearized between the TEF promoter and the toxin indicated that growth was enabled because of a dramatic recombination event between one of the linear ends and a related sequence in the vector. Based on the recombination efficiencies, it can be concluded that the illegitimate recombination event for closing of the vector bearing the TEF promoter is significantly less frequent than intraplasmid recombination between the two actin promoters. Together with the fact that fidelity of recombination is not affected by use of the TEF promoter, it should be emphasized that background in region replacements using homologous recombination is minimal (less than 0.5%) if the γ-toxin negative selection marker is under control of the heterologous TEF promoter and if the target vector is linearized between the TEF promoter and the γ-toxin.

In the scope of the present invention, homologous recombination has been used for replacement of the CDR3VL of a prototype single chain. In contrast to other studies (Hua, Luo et al. 1998), (Zhu and Hua 2002), the *Kluyveromyces lactis* killer toxin γ-subunit has been included in the target vector to counterselect clones that do not integrate the donor DNA correctly. The negative marker was inserted into the target vector instead of the sequence to be replaced. The linearized target vector and the accordingly designed donor DNA were co-transformed into a Wt yeast strain, the total number of transformants per microgram vector DNA and the recombination efficiency calculated. The numbers were determined for target vectors with the γ-toxin under control of either an endogenous *S. cerevisiae* or a heterologous promoter and compared to homologous recombination without the negative selection. It was found that the maximal, number of transformants was decreased from 620'000 to 400'000 when the negative marker was included. On the other hand, the recombination efficiency was increased from 59 to 138 for use of the endogenous yeast promoter and to 302 in combination of the γ-toxin with the heterologous TEF promoter from *Ashbya gossypii*. On one hand, these data show that homologous recombination is highly efficient and can be used for production of libraries with a complexity of few millions of independent clones. On the other hand, the results clearly demonstrate the usefulness of the γ-toxin as a negative selection marker for minimizing the number of background clones. They also emphasize the importance of using a heterologous promoter for expression of the γ-toxin. It should be noted that not only the TEF promoter is suitable for this application, but that any other strong heterologous promoter functional in *S. cerevisiae* will serve the purpose. With use of a heterologous promoter, background can be kept as low as 0.3%, which is significantly below what is expected for either traditional library production with cloning (5%) or library production using straight homologous recombination (1.7% in our hands). In order to facilitate experimental handling, use of the uncut, circular vector as target sequence can be envisioned.

Materials and Methods

Yeast Media, Strains, and Genetic Techniques

Strains without plasmids were grown in complete medium YPAD (2% (w/v) glucose, 2% (w/v) peptone, 1% (w/v) yeast extract, 40 µg/ml adenine sulfate, 2% (w/v) agar for solid medium). Strains bearing plasmids were selected on yeast nitrogen base (YNB) minimal medium containing the required nutritional supplements (Guthrie and Fink 2002). For galactose induction experiments, selective plates containing 2% (w/v) galactose, 2% (w/v) raffinose, 1% (w/v) glycerol, and the required nutritional supplements were used (Guthrie and Fink 2002). Standard transformation of yeast cells was accomplished using the high efficiency lithium acetate method (Woods and Gietz 2001).

The yeast strains used were JPY5 (Matα leu2 ura3 trp1 his3 lys2) (Barberis, Pearlberg et al. 1995) for galactose induction experiments and JPY9 (Matα leu2 ura3 trp1 his3 lys2 gal4Δ) (Barberis, Pearlberg et al. 1995) for all other applications.

DNA Techniques and Plasmid Constructions

All DNA manipulations were performed according to standard techniques (Sambrook and Russell 2001). Restriction enzymes, calf intestine phosphatase (CIP), T4 DNA polymerase, and T4 DNA ligase were purchased from New England Biolabs or Invitrogen. All PCRs for cloning purposes were performed with a DNA polymerase with proofreading activity (Vent, New England Biolabs). Purification of DNA fragments was performed with the QIAquick Gel Extraction kit from Qiagen; plasmids were purified using the Wizard Plus Miniprep kit from Promega. Oligonucleotides were synthesized by Microsynth GmbH and by Invitrogen.

The γ-subunit of the *Kluyveromyces lactis* killer toxin (γ-toxin) was cloned as four separate fragments based on the presence of suitable restriction sites. Three of the four fragments were either produced by annealing of complementary oligonucleotides followed by cloning into pBS or by annealing of partially overlapping oligonucleotides followed by a fill-in reaction with T4 DNA polymerase and subsequent cloning into pBS. For production of the fourth fragment, three independent, partially overlapping smaller fragments were produced by annealing of oligonucleotides followed by a fill-in reaction with T4 DNA polymerase. The resulting three fragments were then co-transformed into yeast together with a, target vector of choice resulting in generation of the larger fragment by homologous recombination. For production of pCS116, the four fragments were removed from their original cloning vectors with restriction enzymes present within the coding sequence of the γ-toxin and cloned sequentially into pBS such as to preserve the coding sequence. The γ-toxin lacking the signal peptide was amplified from pCS116 with a 5' oligonucleotide bearing an XhoI site and a 3' oligonucleotide bearing a NotI site for cloning into pMH5 resulting in pCS118. For construction of pCS131, pCS133, and pCS135, the γ-toxin together, with TGAL11 was released from pCS118 with XhoI and HindIII and cloned into pMH3, pMH4, or pDU10, respectively. PTEF was amplified from pFA6a-kanMX4 (Wach et al.) with a 5' oligonucleotide bearing an EcoRI site and a 3' oligonucleotide bearing an XbaI site and cloned into pMH5 such as to replace PADHf1 resulting in plasmid pCS137. For construction of pCS140, the γ-toxin together with TGAL11 was released from pCS118 with XhoI and HindIII and cloned into pCS137. For generation of pCS136 and pCS143, the γ-toxin together with the corresponding promoter was amplified with a 5' oligonucleotide bearing homologies to the region upstream of the PstI site found immediately 5' of the CDR3L and to the C-terminus of the γ-toxin and a 3' oligonucleotide bearing homologies to the corresponding promoter and to the region downstream of the BamHI site found immediately 3' of the CDR3L. The such generated PCR fragment was co-transformed with pVKS1/25 linearized with PstI and BamHI into yeast, and clones growing at 37° C., but not at 24° C., were selected. Correct integration of the promoter/γ-toxin fusion was confirmed by restriction analysis and sequencing.

Homologous Recombination and Analysis of Resulting Clones

For the purpose of homologous recombination, the target vector of choice was linearized with the indicated restriction enzyme(s), treated with CIP; and purified over a Qiagen DNA column. The donor fragment used for homologous recombination was designed on one hand such as to include the PstI-BamHI sequence of the single chain (scFv) light chain, which spans the CDR3. On the other hand, 40 basepairs (bp) or 60 bp homologous to the scFv sequence immediately 5' of the PstI site or immediately 3' of the BamHI site, respectively, were added to the 5' and to the 3' end of the donor fragment for efficient homologous recombination. The donor fragment was generated by PCR using oligonucleotides CDR3f_40 (5' CAG TGG ATC TGG GAC AGA AT) (Seq. Id. No. 1) and CDR3r_60 (5' GAG TCT CAG GGA CCC CCC AG) (Seq. Id. No. 2) and pVKS1/25 as template. The resulting product was digested with DpnI to remove parental DNA and purified over a Qiagen DNA column. The concentration of both target vector(s) and donor PCR fragment was determined on an agarose gel-using a marker reference (2-log DNA ladder, New England Biolabs). For co-transformation of target and donor DNA into yeast, 100 µg of target vector and a 40× molar excess of PCR donor fragment were combined. When used for homologous recombination, an optimized high efficiency lithium acetate transformation protocol was used. The strain JPY9 was harvested at a cell density of $4\times10^7$. Resuspension volumes were adjusted accordingly, and 50 µl of the cells competent for transformation were used for each single transformation. Heat shock time was increased to 40 minutes. All other parameters were according to (Woods and Gietz 2001).

For analysis of the growing clones, a PCR with oligonucleotides CDR3f_40 (Seq. Id. No. 1) and CDR3r_60 (Seq. Id. No. 2) was performed directly on the yeast clones. The resulting PCR product was on one hand analyzed on an agarose gel and on the other hand subjected to restriction analysis with PstI and BamHI. This procedure allowed a direct assessment of the recombination event and the sequence at the recombination junction. In addition, plasmids were rescued from individual transformants and the region modified during homologous recombination was sequenced.

Spotting Assay

Strains were grown to saturation in selective medium at 37° C. and cell density was determined. The cultures were then diluted to $5\times10^6$ cells/ml, $1.5\times10^6$ cells/ml, $5\times10^5$ cells/ml, $1.5\times10^5$ cells/ml, and $5\times10^4$ cells/ml in sterile water. 5 µl of each serial dilution corresponding to 25'000, 7575, 2500, 757, or 250 cells, respectively, were spotted onto selective glucose and/or galactose plates. Plates were then incubated at 24° C. for two days, at 30° C. for 1.5 days, and at 37° C. for 1 day.

While there are shown and described presently preferred embodiments of the invention, it is to be distinctly understood that the invention is not limited thereto but may be otherwise variously embodied and practiced within the scope of the following claims.

Takita, M. A. and B. Castilho-Valavicius (1993). "Absence of cell wall chitin in *Saccharomyces cerevisiae* leads to resistance to *Kluyveromyces lactis* killer toxin." *Yeast* 9(6): 589-98.

Wach, A. (1996). "PCR-synthesis of marker cassettes with long flanking homology regions for gene disruptions in *S. cerevisiae.*" *Yeast* 12(3): 259-65.

Woods, R. A. and R. D. Gietz (2001). "High-efficiency transformation of plasmid DNA into yeast."*Methods Mol Biol* 177: 85-97.

Zhu, L. and S. B. Hua (2002). Generation of highly diverse library of expression vectors via homologous recombination in yeast. U.S. Pat. No. 6,410,271.

```
SEQUENCE LISTING

<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: PCR Primer

<400> SEQUENCE: 1
cagtggatct gggacagaat                                                20

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
gagtctcagg gacccccag                                                 20
```

REFERENCES

Barberis, A., J. Pearlberg, et al. (1995). "Contact with a component of the polymerase II holoenzyme suffices for gene activation." *Cell* 81(3): 359-68.

Butler, A. R., J. H. White, et al. (1994). "Two *Saccharomyces cerevisiae* genes which control sensitivity to G1 arrest induced by *Kluyveromyces lactis* toxin." *Mol Cell Biol* 14(9): 6306-16.

Butler, A. R., J. H. White, et al. (1991). "Analysis of the response of *Saccharomyces cerevisiae* cells to *Kluyveromyces lactis* toxin." *J Gen Microbiol* 137(Pt 7): 1749-57.

Guthrie, C. and G. R. Fink (2002). *Guide to yeast genetics and molecular and cell biology*. San Diego, Academic Press.

Hua, S. B., Y. Luo, et al. (1998). "Construction of a modular yeast two-hybrid cDNA library from human EST clones for the human genome protein linkage map."*Gene* 215(1): 143-52.

Sambrook, J. and D. W. Russell (2001). *Molecular Cloning: a laboratory manual*. New York, Cold Spring Harbor Laboratory Press.

The invention claimed is:

1. A method for the construction of randomized gene libraries in yeast cells sensitive to *Kluyveromyces lactis* γ toxin and which are capable of homologous recombination comprising the following steps:

introducing into said yeast cells a) a target vector comprising a first DNA sequence coding for at least a γ-subunit of a *Kluyveromyces lactis* killer toxin as negative selection marker, wherein said *Kluyveromyces lactis* killer toxin lacks the signal peptide and wherein said DNA sequence is flanked at its 5' end by a first target sequence and at its 3' end by a second target sequence and;

b) a donor DNA sequence which is flanked at its 5' end by a DNA sequence which is homologous to said first target sequence and flanked at its 3' end by a DNA sequence which is homologous to said second target sequence; and cultivation of said yeast cells under conditions allowing the selection of cells in which said DNA sequence in the target vector encoding at least a γ-subunit of a *Kluyveromyces lactis* killer toxin has been replaced by said donor sequence by means of homologous recombination thereby abolishing expression of said γ-subunit of a *K. lactis* killer toxin.

2. The method of claim 1, wherein said target vector further comprises a second DNA sequence encoding at least one protein region.

3. The method of claim 2 wherein said first DNA sequence of said target vector flanked by said two target sequences is present within a protein region encoding DNA sequence of said second DNA sequence comprised in said target vector.

4. The method of claim 1 wherein said DNA sequence encoding at least the γ subunit of the *K. lactis* killer toxin is under control of a heterologous promoter.

5. The method of claim 4 wherein said promoter is located between the DNA sequence encoding at least the γ subunit of *K. lactis* killer toxin and one of the two target sequences.

6. The method of claim 1, wherein said first DNA sequence of said target vector comprises at least one restriction enzyme recognition site that is unique for a given restriction enzyme.

7. The method of claim 6, wherein said unique recognition site is located in the coding region of the γ-toxin DNA sequence.

8. The method of claim 2 wherein said second DNA sequence encodes an antibody or a single chain antibody.

9. The method of claim 3 wherein said second DNA sequence encodes an antibody or a single chain antibody and wherein said first DNA sequence of said target vector present within at least one CDR encoding region of said antibody or said single chain antibody.

10. The method of claim 8 or 9 wherein said first DNA sequence comprising the γ subunit of *K. lactis* killer toxin is transcribed in the opposite direction of said antibody or single chain antibody gene.

11. The method of claim 1 wherein said target vector is introduced into said yeast cells in linearized form.

12. The method of claim 11 wherein said target vector is linearized by cutting with a restriction enzyme recognizing in said first DNA sequence of said target vector said at least one restriction enzyme recognition site that is unique for a given restriction enzyme.

13. The method of claim 1 wherein said donor sequence comprises a DNA sequence encoding a protein region.

14. The method of claim 1 wherein said target vector and said donor sequence are introduced into said yeast cells by co-transformation.

15. The method of claim 1 wherein said yeast cells are cultivated at a temperature selected from the range of 24° C. to 30° C.

16. The method of claim 4 wherein the promoter is a constitutive promoter.

17. The method of claim 4 wherein the promoter is a TEF promoter from *Ashbya gossypii*.

18. The method of claim 6 wherein the restriction enzyme recognition site that is unique for a given restriction enzyme is located between the coding region of the γ-toxin DNA sequence and the promoter.

19. The method of claim 9 wherein the first DNA sequence of said target vector replaces a CDR3VL region of said antibody or said single chain antibody.

20. The method of claim 9 wherein the first DNA sequence of said target vector replaces a CDR2 and a CDR3 region of said antibody or said single chain antibody.

21. The method of claim 1 wherein said yeast cells are *Saccharomyces cerevisiae* cells.

22. The method of claim 13 wherein said donor sequence comprises a DNA sequence encoding a CDR region of an antibody.

23. The method of claim 2, wherein said second DNA sequence encodes more than two protein regions.

24. The method of claim 2 wherein said second DNA sequence encodes a full length protein.

25. The method of claim 13 wherein said protein region is a CDR region of an antibody.

* * * * *